| United States Patent [19] | [11] | Patent Number: | 5,071,653 |
|---|---|---|---|
| Kakuda et al. | [45] | Date of Patent: | Dec. 10, 1991 |

[54] *CAMELLIA SINENSIS* EXTRACTS THAT PROMOTE THE GROWTH OF BIFIDOBACTERIUM

[75] Inventors: Takami Kakuda, Shizuoka, Japan; Robert M. Parkhurst, Redwood City, Calif.

[73] Assignee: Itoen Ltd., Tokyo, Japan

[21] Appl. No.: 308,736

[22] Filed: Feb. 9, 1989

[51] Int. Cl.$^5$ ............................................. A61K 35/78
[52] U.S. Cl. .................... 424/195.1; 426/435; 426/597
[58] Field of Search ............... 424/195.1; 426/435, 426/597

[56] References Cited

U.S. PATENT DOCUMENTS

| 1,520,122 | 2/1923 | Gephart et al. | 426/597 |
| 2,697,663 | 12/1954 | Tomarelli et al. | 426/71 |
| 2,872,382 | 2/1959 | Keck | 426/601 |
| 3,155,523 | 11/1964 | Reich | 426/430 |
| 3,163,539 | 12/1964 | Barch et al. | 426/385 |
| 3,532,506 | 10/1970 | Rey et al. | 426/594 |
| 4,048,344 | 9/1977 | Gasser et al. | 426/385 |
| 4,130,669 | 12/1978 | Gregg | 426/385 |

*Primary Examiner*—John W. Rollins
*Attorney, Agent, or Firm*—Morrison & Foerster

[57] ABSTRACT

Substantially flavorless extracts from the leaves of *C. sinensis* are provided which promote the growth of Bifidobacterium. Compositions are provided by extracting water or ethanol-soluble solids from *C. sinensis* leaves with a polar organic solvent that is immiscible with water.

25 Claims, No Drawings

CAMELLIA SINENSIS EXTRACTS THAT PROMOTE THE GROWTH OF BIFIDOBACTERIUM

TECHNICAL FIELD

The present invention relates to extracts of *Camellia sinensis* and methods of promoting the growth of Bifidobacterium.

BACKGROUND

Bifidobacterium have long been recognized as a desirable resident of the mammalian digestive tract. Colonization of the gut by these bacteria is believed to occupy niches that might otherwise be filled by pathogenic microorganisms, particularly gram negative bacteria. Bifidobacterium are also believed to produce many products, such as vitamins, which are beneficial to the host. Promoting the growth of Bifidobacterium in human infants in particular has been recognized as being important to the development of disease resistance. See, e.g., U.S. Pat. No. 2,697,663; U.S. Pat. No. 2,872,382.

In order to enhance colonization of the human intestinal tract by Bifidobacterium, a number of products have been developed. For example, live bacteria have been marketed as a medicine or foodstuff. This approach is disadvantageous, however, because the bacteria must be maintained in a viable state. Furthermore, bacteria exogenous to the host often have difficulty in colonization because of competition with native microorganisms. Another approach has been to market sugars, such as fructose oligosaccharides, which are among the beneficial compounds produced by Bifidobacterium. This approach is also undesirable, however, since the manufacture of these compounds is relatively expensive and high dosages are required to achieve an effect comparable to enhanced colonization by Bifidobacterium. Nor does this administration of the these compounds protect the host from colonization by pathogens.

Instant tea has been prepared by a number of methods, typically involving spray drying a hot water infusion of the tea. A primary goal of these techniques is to retain the flavor of the liquid tea drink. U.S. Pat. No. 1,520,122, describes evaporating a water infusion of tea to dryness at low pressure, treating the distillate with a solvent to recover aroma and flavor compounds, and then reintroducing these compounds to the solids recovered from the water infusion. U.S. Pat. No. 3,532,506 is directed to extracts from coffee, tea or chicory where an aqueous extract and a liquid carbon dioxide extract are combined prior to freeze-drying the material. U.S. Pat. No. 3,163,539 is directed to an instant tea composition wherein a water extract is treated with oxygen under alkaline conditions to increase the proportion of cold water-soluble solids. U.S. Pat. No. 4,048,344 is directed to a continuous method of making an aqueous tea extract and freeze-drying the resulting material. U.S. Pat. No. 4,130,669 is directed to a steam extraction of tea, followed by freeze-drying the extract. A tea volatile concentrate is prepared by contacting frozen condensate with the aqueous tea extract.

A continuing need exists for improved methods of promoting the growth of Bifidobacterium in mammalian hosts, such as humans. It would be particularly desirable if a method could be developed that does not require the use of live bacteria, or the use of expensive, high-dosage products. It would also be extremely desirable if any product developed would not have any strong flavor, so that it could be readily formulated with a variety of foods.

SUMMARY OF THE INVENTION

It has been surprisingly discovered that a substantially flavorless extract of Camellia sinensis can be prepared which has substantial Bifidobacterium growth-promoting properties. Furthermore, the extract can be prepared inexpensively relative to other products used to promote the growth of Bifidobacterium. Particularly important is the lack of any strong flavor in the extract so that it is readily compatible with a great number of foods. Alternatively, the extract can be formulated into a direct dietary supplement, such as a tablet or capsule.

One embodiment of the present invention is directed to a method of preparing an extract of *C. sinensis* having Bifidobacterium growth-promoting properties comprising: (a) extracting *C. sinensis* leaves with water or a water-miscible organic solvent to provide a solution comprising dissolved solids; (b) extracting an aqueous solution of said dissolved solids with a polar organic solvent immiscible with water to provide an organic phase and an aqueous phase; and (c) recovering the dissolved solids in said aqueous phase.

In another embodiment, the present invention is directed to a method of preparing an extract from *C. sinensis* having Bifidobacterium growth-promoting properties comprising: (a) extracting *C. sinensis* leaves with hot water to provide an aqueous leaf extract and leaf residue; (b) extracting an aqueous crude product with at least one polar organic solvent immiscible with water to provide an organic solvent phase and an aqueous product phase, wherein said aqueous crude product is an aqueous solution comprising dissolved crude solids, said dissolved crude solids being selected from the group consisting of the dissolved solids in said aqueous leaf extract and the dissolved solids obtained from an extraction of said leaf residue with a water-miscible organic solvent; and (c) recovering the dissolved solids in said aqueous product phase.

In other embodiments, the present invention is directed to solid compositions prepared by the above methods. The present invention is also directed to a substantially flavorless composition that promotes the growth of Bifidobacterium comprising the water-soluble solids of *C. sinensis* leaves substantially free of the solids that are also soluble in a water-immiscible polar organic solvent.

These and other embodiments of the present invention will be readily apparent to those skilled in the art from the following description.

DETAILED DESCRIPTION

*Camellia sinensis* (also called *Thea Camellia sinensis*) is an evergreen native to southeastern Asia. Tea is made from its leaves. Extracts of the present invention are also prepared from *C. sinensis* leaves, whether fresh or processed (e.g., tea). Due to the commercial abundance of teas, however, it is preferred to use a tea as the starting material in the practice of the present invention. Any *C. sinensis* tea is suitable as a starting material, including fermented tea (black tea), semifermented tea (Oolong tea), or green tea (e.g., Sencha or Gyokuro).

In the practice of the invention, a crude liquid extract is first prepared. The tea can be extracted with either water, a water-miscible organic solvent, or both to prepare the first crude fraction. Preferred water-miscible solvents are polar, and include alcohols, such as methanol, ethanol, n-propanol, i-propanol, or tert-butanol. Typically the water or solvent will be heated or boiled. It may be desirable to exclude oxygen during this extraction step. This can be done, for example, by bubbling an inert gas (e.g., nitrogen, argon, etc.) through the liquid during the extraction process.

In the typical practice of the present invention, a hot water extract is made by boiling the *C. sinensis* leaves for about 5 minutes to about 2 hours, or preferably until substantially all of the water-soluble solids are dissolved. A cold water infusion may also be used, but the extraction will take considerably longer. The water phase is then separated from the leaf residue to provide a crude aqueous product. It is preferred to concentrate the dissolved solids in the crude aqueous phase., for example, by freeze-drying to provide a solid crude product. The leaf residue can also be extracted again, this time with a water-miscible organic solvent, as described above (preferably ethanol) for about 5 minutes to about 2 hours. The organic solvent phase is then separated from the leaf residue and the dissolved solids recovered, preferably by evaporation to dryness.

The crude product prepared by water or solvent extraction is then typically redissolved in water and extracted with a water-immiscible polar organic solvent. Examples of such solvents include n-butanol, pentanol, hexanol, chloroform, and ethyl acetate. The aqueous solution can be extracted with only one such solvent, or more than one in a sequential manner. Particularly in the case of a single extraction, however, the preferred solvent is n-butanol.

The aqueous phase after the above solvent extraction and the dissolved solids contained therein are then recovered by separating the aqueous phase from the organic phase. Preferably, the recovery also includes isolating the dissolved solids by, for example, evaporation or freeze-drying. It is believed that the solids in the final product are comprised primarily of the water-soluble solids of *C. sinensis* leaves, substantially free of the water-soluble solids that are also soluble in polar organic solvents. The resulting fraction of water-soluble solids is substantially flavorless relative to tea or instant tea extracts. This relative lack of flavor can be judged by using a taste panel, preferably an expert panel, using standard controls. The aqueous phase can be used as-is, concentrated, or the solids recovered (e.g., freeze-drying) to provide a solid product.

The solids recovered in or from the aqueous phase after the organic solvent extraction can be employed to promote Bifidobacteria growth either in vitro or in vivo. All that is required is for an effective amount of the solids to be brought into contact with the bacteria. For example, the solids can be used as a supplement to a growth medium in the commercial production of Bifidobacterium. Examples of such bacteria include *B. adolescentis, B. longum, B. bifidum, B. breve,* and *B. infantis*. For in vivo application, the solids could be formulated into a tablet for direct administration, or incorporated into a food product, such as cereal or drink mixes. The aqueous phase containing the products could also be directly formulated into processed foods. The appropriate dosages and concentrations will vary over a wide range, but can be readily determined by those of ordinary skill in the art through routine screening. An effective amount to promote the growth of Bifidobacterium can be determined, for example, by screening the growth rate in the assay described below.

The present invention will be more fully illustrated below by the following examples. These examples are provided for illustrative purposes only and are not intended to limit the scope of the claims in any manner.

EXAMPLES

Extract Preparation

The extracts tested below were generally prepared according to the following method, which will be referred to as "Method 1." First, 400 g. of tea leaves were boiled in 3000 ml of distilled water for 1 hour. Argon was bubbled through the water at all times. The mixture was then filtered, and the aqueous solution freeze-dried to provide a powder referred to below as the "crude water" extract. The tea leaf residue was then extracted with ethanol by treating the residue with 2000 ml of ethanol at boiling for 1 hour. The ethanol extract was evaporated to provide a powder, referred to below as the "crude ethanol" extract.

In the next step, 2.5 g. of either the crude water extract or crude ethanol extract was dissolved in 500 ml of distilled water, and extracted twice with 250 ml of chloroform (total 500 ml chloroform). The chloroform extract was evaporated to a powder, called the "water/chloroform" or "ethanol/chloroform" extract, depending upon whether the starting material was the crude water extract or the crude ethanol extract, respectively. The aqueous phase was then extracted again with ethyl acetate (250 ml twice, total 500 ml) The ethyl acetate phase was evaporated to a powder, referred to as either the "water/ ethyl acetate" or "ethanol/ethyl acetate" extract. The aqueous phase was again extracted, this time with butanol (250 ml twice, total 500 ml), and the butanol phase evaporated to a low volume of oily residue. About 100-200 ml of distilled water was added to the oily residue, and then freeze-dried to provide a powder, referred to as the "water/butanol" or "ethanol/butanol" extract. The final aqueous phase was freeze-dried to a powder, which is the final product. This product is referred to as either the "water/water" extract, or the "ethanol/water" extract.

In an alternative method, referred to as "Method 2," the crude water extract was extracted with organic solvents as described above, with the exception that only butanol was used. The aqueous phase was separated from the butanol phase and freeze-dried to a powder, which is referred to as a "$H_2O$/butanol/$H_2O$" extract.

Extract Analysis

Various extracts described above were further fractionated for analysis in Bifidobacterium growth experiments. First, an ash fraction was prepared by burning 50 mg of a water/water extract in an electric oven at 580° C. for two hrs, followed by overnight cooling. The resulting product was still dark, so it was again burned at 580° C. for two hrs. The resulting ash was then dissolved in 500 ml distilled water for the test described below.

Aqueous solutions of water/water extract were also fractionated by passage over several resins. Fifty milligrams of water/water extract in 1 ml distilled water was passed through a column of resin, and up to 5 ml of eluant was collected. Three different resins were used, to produce three different fractions: Dowex A-I chelating resin ("chelating resin" extract), BioRad A6-1-X8 quaternary ammonium (OH) resin ("QA resin" extract), and BioRad A6-50W-X2 sulfonic acid (H) resin ("SO$_3$H resin" extract).

Bacterial Growth Assay

Five Bifidobacterium species were obtained from the ATCC: *B. adolescentis, B. longum, B. bifidum, B. breve,* and *B. infantis.* Two growth media were used, the first is brain heart infusion broth (BHI) available from Anaerobe Systems (San Jose, California) The second is glucose-mineral salts-biotin media (GMB), as described at page 145 of Anaerobe Laboratory Manual, (Fourth edition). GMB comprises glucose (1.0 g.), (NH$_4$)$_2$SO$_4$ (0.1 g.), distilled water (96.0 ml), salts solution (4.0 ml Earle's Basic Salt Solution), resazurin solution (0.4 ml; 0.025% w/v), biotin (0.4 ml; 0.125 mg/10 ml), cysteine (0.05 g. added after boiling), and NaHCO$_3$ (0.5 g. added after boiling).

At first, BHI medium was used to grow bacteria. Proliferation of Bifidobacteria on this medium, however, was too fast, making the measurement of proliferation rates difficult. Consequently, GMB medium was tried as the basic medium, and a GMB-2 medium having salt concentrations one half of those in GMB was also prepared. GMB-2 medium was well suited for all of the Bifidobacterium with the exception of *B. bifidum.* For *B. bifidum*, however, the addition of BHI medium at a rate of 1-5% (w/w) was necessary.

Samples of extracts or other compositions for growth promoting screening were used to prepare stock solutions by dissolving the extracts or compositions in GMB-2 media. The highest concentrations for various extracts in the stock solutions ranged from 1.0% (w/v) to 2.5% (w/v). In the assay, sufficient stock solution (e.g., stock solution of water/water extract in GMB-2) was added to 4 ml of GMB-2 culture media to provide for the desired final concentration in the culture medium. Fifty microliters of inoculant (overnight culture on BHI) was then added to the culture media. The cultures were incubated at 37° C. overnight (two nights in the case of *B. infantis*) under anaerobic conditions. The cultures were then centrifuged at 10,000 rpm for 15 minutes. The resulting pellet was dissolved in 4 ml of phosphate buffered saline, and the optical density (O.D.) reading was taken at 650 nm. All assays were performed in duplicate, and the optical density readings averaged.

Results

I. Green Tea Crude Extracts

Green tea crude extracts were prepared according to Method 1 from Sencha (green tea) and Gyokuro (refined green tea). Both extracts exhibited superior growth-promoting activity with B. adolescentis in the above-described growth assay at or above a minimum concentration of about 0.0025% (w/v) as shown in Table 1.

TABLE 1

Growth Promotion of *B. adolescentis* with Crude Water Extract of Sencha

| Sample | OD Reading |
|---|---|
| Bacteria Control | 0.05 |
| 0.05% w/v | 0.27+ |
| 0.0125 | 0.17+ |
| 0.0025 | 0.13+ |
| 0.00125 | 0.08± |
| 0.000125 | 0.06− |

Eight Sencha extracts, obtained according to Method 1, were prepared. The abbreviated names and collected amounts for each extract are shown in Table 2. The Sencha extracts were tested in the above assay with *B. adolescentis*. As shown in Table 3, highest growth promoting activity was observed with the water/ water and ethanol/water extracts. The concentration dependence of the activities in these two extracts was investigated and both exhibited superior activity above a minimum concentration of about 0.0025% (w/v), as shown in Table 4.

TABLE 2

Fractionation and Yield

| Extract | SENCHA | Yield | GYOKURO | Yield | OOLONG | Yield |
|---|---|---|---|---|---|---|
| Water/water | S-W/W | 1368.6 mg | G-W/W | 1436.6 mg | O-W/W | 1320.2 mg |
| Water/Butanol | S-W/B | 379.1 | G-W/B | 213.9 | O-W/B | 359.9 |
| Ethanol/Butanol | S-E/B | 967.0 | | | O-E/B | 600 |
| Ethanol/Water | S-E/W | 448.9 | | | O-E/W | 380.0 |
| Water/Chloroform | S-W/C | 321.0 | G-W/C | 260.6 | O-W/C | 161.7 |
| Ethanol/Chloroform | S-E/C | 248.1 | | | O-E/C | 410.7 |
| Water/Ethyl acetate | S-W/EA | 518.7 | G-W/EA | 320.1 | O-W/EA | 338.7 |
| Ethanol/Ethyl acetate | S-E/EA | 678.5 | | | O-E/EA | 720.0 |

TABLE 3

Growth Promotion of *B. adolescentis* with Eight Sencha Extracts

| Sample | OD Reading |
|---|---|
| Bacteria Control | 0.08 |
| Sencha-W/W (0.025% w/v) | 0.27+ |
| W/B | 0.05− |
| E/B | 0.07− |
| E/W | 0.29+ |
| W/C | 0.10± |
| E/C | 0.06− |
| W/EA | 0.07− |
| E/EA | 0.08− |

TABLE 4

Growth Promotion of *B. adolescentis* with Different Concentration of Sencha Water/Water and Ethanol/Water Fraction

| Sample and Concentration | Water/water | OD Reading Ethanol/water |
|---|---|---|
| Bacteria Control | 0.06 | |
| 0.025% w/v | 0.45+ | 0.38+ |
| 0.0125 | 0.32+ | 0.26+ |
| 0.0025 | 0.16+ | 0.16+ |
| 0.00025 | 0.08− | 0.09− |

II. Comparison of Green and Oolong teas

Extracts of Sencha, Gyokuro and Oolong were prepared according to Method 1, the yields being shown in Table 2. The various extracts were tested in the above assay with *B. adolescentis*. As shown in Table 5, all exhibited high growth-promoting activity for the water/water extract above the same minimum concentration of 0.0025% (w/v). As shown in Table 6, Oolong tea extracts exhibited activity similar to Sencha extracts, including the water/water and ethanol/water extracts.

TABLE 5

Growth Promotion of *B. adolescentis* with Different Concentration in Green Tea (Sencha and Gyokuro) and Half Fermented Tea (Oolong)

| Sample and Concentration | OD Reading Gyokuro-W/W | Sencha-W/W | Oolong-W/W |
|---|---|---|---|
| Bacteria Control | | 0.06 | |
| 0.025% w/v | 0.44+ | 0.45+ | 0.33+ |
| 0.0125 | 0.33+ | 0.32+ | 0.31+ |
| 0.0025 | 0.17+ | 0.16+ | 0.17+ |
| 0.00025 | 0.07− | 0.08− | 0.11± |

TABLE 6

Growth Promotion of *B. adolescentis* with Eight Oolong Fractions

| | OD |
|---|---|
| Bacteria control | 0.02 |
| O-W/W (0.025%) | 0.21+ |
| O-W/B | 0.05− |
| O-E/B | 0.02− |
| O-E/W | 0.19+ |
| O-W/C | 0.03− |
| O-E/C | 0.1*− |
| O-W/EA | 0.02− |
| O-E/EA | 0.04− |

*O.D. due to dissolved compounds, not bacteria.

III. Growth Promoting Activity of Inorganic Compounds

Incineration products (inorganic compounds) of Sencha, Gyokuro and Oolong teas were tested as growth promoters in the above assay using *adolescentis*. The incineration products obtained as described above all showed approximately half the activity of the positive control (Gyokuro-water/water extract) at a minimum of 0.025% (w/v), as shown in Table 7.

TABLE 7

Growth Promotion of *B. adolescentis* with Ash from Water/Water Extract of Sencha, Gyokuro and Oolong

| | OD |
|---|---|
| Bacteria control | 0.02 |
| Positive control (G-w/w 0.025% w/v) | 0.29 |
| S-w/w-Ash (10° = 0.025% w/v) | 0.16 |
| G-w/w-Ash (10° = 0.025% w/v) | 0.16 |
| O-w/w-Ash (10° = 0.025% w/v) | 0.16 |

A trial testing the growth promotion properties of inorganic compounds and chelating resin-treated extracts was carried out with adolescentis. Since growth promotion by inorganic compounds was suggested by the data in Table 7, an analysis of the inorganic compounds in the Gyokuro-water/water extract was performed. Six metals (aluminum, calcium, magnesium, manganese, phosphorus and sodium) were present in large quantities. Since the tea leaves also contained large quantities of potassium, the seven metal salts shown in Table 8 were tested. Phosphorus and potassium showed approximately half the activity of the positive control (Gyokuro-water/ water). When the seven metal salts were mixed in equal quantities and the mixture used at the same combined concentration as the individual salts, the activity of the mixture was higher than that of any of the salts individually even though the concentration of each of the salts was reduced seven-fold. Inorganic compounds were removed from the water/water extract with a chelating resin as described above. As shown in Table 8, the resulting extract did not show any significant activity. If the metal salt mixture was added to the extract absorbed with the chelating resin, activity was raised to the same level as the positive control. (Gyokuro-water/water).

TABLE 8

Growth Promotion of *B. adolescentis* with Inorganic and Organic Compounds

| Sample and Concentration | OD Reading |
|---|---|
| Bacteria control | 0.04 |
| Positive control (G-W/W 0.025% w/v) | 0.36 |
| Al (AlNH$_4$(SO$_4$)$_2$.12H$_2$O) 0.025% w/v | 0.07+ |
| Ca (Ca(acetate)$_2$.H$_2$O) | 0.01− |
| Mg (MgSO$_4$.7H$_2$O) | 0.01− |
| Mn (MnSO$_4$.H$_2$O) | 0.02− |
| P (NaHPO$_4$.H$_2$O) | 0.15+ |
| Na (Na cit.2H$_2$O) | 0.01− |
| K (KCL) | 0.16+ |
| Mixture of above compounds 0.025% w/v | 0.22+ |
| Chelating Resin Ext. (organic chemical) 0.025% w/v | 0.05− |
| Mixture + Chelating 0.025% w/v | 0.37+ |

A comparison of the growth promoting properties of extracts absorbed with quaternary ammonium (OH) and sulfonic acid (H) resins with *adolescentis* was also carried out. The results are shown in Table 9. Some low activity was exhibited with quaternary ammonium (OH) resin-treated extract. When this treated extract was mixed with the extract treated with the chelating resin, activity was increased.

TABLE 9

Growth Promotion of *B. adolescentis* with QA-Resin Extract, SO$_3$H Resin Extract and Chelating Resin Extract

| | OD |
|---|---|
| Bacteria control | 0.04 |
| Positive control (G-w/w 0.025% w/v) | 0.26+ |
| QA-Resin Ext. | 0.10+ |
| SO$_3$H-Resin Ext. | 0.06− |
| Chelating Resin Ext. | 0.05− |
| QA-Resin Ext. + Chelating Resin Ext. | 0.14+ |
| SO$_3$H-Resin Ext. + Chelating Resin Ext. | 0.06− |

IV. Butanol Extraction

A comparison of the water/water extract with a simple butanol extract made by Method 2 was carried out with *B. adolescentis*. The growth promoting activities of the water/water and the H$_2$O/ButOH/H$_2$O extracts are shown in Table 10. Almost the same level of activity was observed.

TABLE 10

Growth Promotion of *B. adolescentis* with Gyokuro H$_2$O/ButOH/H$_2$O and Gyokuro Water/Water Extracts

| | OD |
|---|---|
| Bacteria control | 0.04 |
| G-H$_2$O/ButOH/H$_2$O | 0.24 |
| G-Water/Water | 0.26 |

V. Growth Promotion of *B. longum, B. bifidum, B. breve* and *B. infantis*

The above species were used to screen for growth promoting properties in various tea extracts, as described above for *B. adolescentis*. The results are shown in Table 11 for *B. longum*, Table 12 for *B. bifidum*, Table 13 for *B. breve*, and Table 14 for *B. infantis*. For all four species of Bifidobacterium, growth promoting activity was observed with the water/ water and ethanol/water extracts of Sencha. The tendency for higher activity with Gyokuro relative to Sencha was observed. Bacteria were susceptible to growth rate promotion at different levels. *B. longum* and *B. adolescentis* exhibited the highest growth promotion, *B. bifidum* and *B. breve* exhibited moderate degrees of growth promotion, and *B. infantis* exhibited the lowest level, requiring two days of incubation. The Gyokuro-$H_2O$/-ButOH/$H_2O$ extract exhibited activity in all Bifidobacterium tested.

Weak growth-promoting activity was observed with the incineration products (inorganic compounds) for *B. adolescentis* and *B. bifidum*, but no activity was exhibited with respect to the other bacteria. The inorganic salt mixture showed activity, though low, in each. The quaternary ammonium (OH) extract exhibited activity in all the bacteria The chelating resin-treated extract showed activity only for *B. bifidum* and *B. breve*.

If incineration products, mixtures of inorganic salts, or either the $SO_3H$ or quaternary ammonium (OH) resin-treated extracts were mixed with the chelating resin-treated extract, growth-promoting activity was observed. Thus, the results for these four bacteria were almost the same as those shown for *B. adolescentis*.

TABLE 11

| Growth Promotion of *B. longum* | | |
|---|---|---|
| Name of Samples and Concentration | OD | OD |
| Bacteria control | 0.02 | 0.01 |
| Positive control G-w/w (0.025% w/v) | 0.36 | 0.35+ |
| S-W/W (0.025% w/v) | 0.31 | + |
| S-W/B (0.025% w/v) | 0.11 | + |
| S-E/B (0.025% w/v) | 0.03 | — |
| S-E/W (0.025% w/v) | 0.19 | + |
| S-W/C (0.025% w/v) | | 0.04— |
| S-E/C (0.025% w/v) | | 0.03— |
| S-W/EB (0.025% w/v) | 0.06 | — |
| S-E/EP (0.0125% w/v) | 0.07 | — |
| G$H_2O$/ButOH/$H_2O$ (0.025% w/v) | 0.33 | + |
| G-W/W-QA Resin Ext. | 0.19+ | |
| G-W/W-Chelating Resin Ext. | 0.05— | |
| G-W/W-Ash | 0.06 | — |
| Mixture of inorganic chemical | 0.08 | — |
| G-W/W-QA Resin + G-W/W-Chelating Resin Ext. | | |
| G-W/W-Ash + G-W/W-Chelating Resin Ext. | | 0.15+ |
| Mixture + G-W/W-Chelating Resin Ext. | 0.28 | + |
| G-W/W-$SO_3H$ Resin Ext. | | 0.03— |

TABLE 12

| Growth Promotion of *B. bifidum* | |
|---|---|
| Name of Samples and Concentration | OD |
| Bacteria control | 0.25 |
| Positive control G-w/w (0.025% w/v) | 0.67 |
| S-W/W (0.025% w/v) | 0.35+ |
| S-W/B (0.025% w/v) | 0.08— |
| S-E/B (0.025% w/v) | 0.08— |
| S-E/W (0.025% w/v) | 0.28± |
| S-W/C (0.025% w/v) | 0.15— |
| S-E/C (0.025% w/v) | 0.05— |
| S-W/EA (0.025% w/v) | 0.05— |
| S-E/EA (0.0125% w/v) | 0.08— |
| Gyokuro $H_2O$/ButOH/$H_2O$ (0.025% w/v) | 0.34+ |
| G-W/W-QA Resin Ext. | 0.74+ |
| G-W/W-Chelating Resin Ext. | 0.71+ |
| G-W/W-Ash | 0.34+ |

TABLE 12-continued

| Growth Promotion of *B. bifidum* | |
|---|---|
| Name of Samples and Concentration | OD |
| Mixture of inorganic chemical | 0.39+ |
| G-W/W-QA Resin + G-W/W-Chelating Resin Ext. | 1.06+ |
| G-W/W-Ash + G-W/W-Chelating Resin Ext. | 1.10+ |
| Mixture + G-W/W-Chelating Resin Ext. | 0.72+ |
| G-W/W-$SO_3H$ Resin Ext. | 0.22— |

TABLE 13

| Growth Promotion of *B. breve* | | |
|---|---|---|
| Name of Samples and Concentration | OD | OD |
| Bacteria control | 0.07 | 0.05 |
| Positive control G-w/w (0.025% w/v) | 0.17 | |
| S-W/W (0.025% w/v) | 0.15 | + |
| S-W/B (0.025% w/v) | 0.08 | — |
| S-E/B (0.025% w/v) | | 0.08± |
| S-E/W (0.025% w/v) | 0.17 | + |
| S-W/C (0.025% w/v) | | 0.07— |
| S-E/C (0.025% w/v) | | 0.05— |
| S-W/EA (0.025% w/v) | | 0.06— |
| S-E/EA (0.0125% w/v) | 0.08 | — |
| G$H_2O$/ButOH/$H_2O$ | 0.12 | + |
| G-W/W-Ash | 0.07 | — |
| G-W/W-Chelating Resin Ext. | 0.14 | + |
| Mixture of inorganic chemical | 0.15 | + |
| G-W/W-QA Resin Ext. | | |
| G-W/W-Ash + G-W/W-Chelating Resin Ext. | 0.19 | + |
| Mixture of inorganic chemical + G-W/W-Chelating Resin Ext. | | |
| G-W/W-QA + G-W/W-Chelating Resin Ext. | 0.19 | + |
| G-W/W-$SO_3H$ Resin Ext. + G-W/W-Chelating Resin Ext. | 0.08 | — |

TABLE 14

| Growth Promotion of *B. infantis* | |
|---|---|
| Name of Samples and Concentration | OD |
| Bacteria control | 0.05 |
| Positive control G-w/w (0.0025% w/v) | |
| S-W/W | 0.30+ |
| S-W/B | 0.02— |
| S-E/B | — |
| S-E/W | 0.29+ |
| S-W/C | — |
| S-E/C | — |
| S-W/EA | 0.02— |
| S-E/EA | 0.04— |
| G$H_2O$/ButOH/$H_2O$ | 0.24+ |
| G-W/W-Ash | 0.61+ |
| G-W/W-Chelating Resin Ext. | 0.05— |
| Mixture of inorganic chemical | 0.19+ |
| G-W/W-QA Resin Ext. | 0.71+ |
| G-W/W-Ash + G-W/W-Chelating Resin Ext. | |
| Mixture of inorganic chemical + G-W/W-Chelating Resin Ext. | 0.47+ |
| G-W/W-QA Resin Ext. + G-W/W Chelating Resin Ext. | 0.57+ |
| G-W/W-$SO_3H$ Resin Ext. | |

VI. Comparison to Instant Tea

A comparison of the activities of Gyokuro crude water extract, gyokuro water/water extract and instant ice tea (Lipton) with respect to *B. adolescentis* and *B. longum* was carried out. As shown in Table 15, the Gyokuro water/water extract showed the highest activity.

TABLE 15

| Comparison with Instant Tea | |
|---|---|
| | OD |
| *B. adolescentis* | |
| Bacteria control | 0.04 |
| G-W/W (0.025% w/v) | 0.26 |
| G-W (0.025% w/v) | 0.22 |
| Instant tea (0.025% w/v) | 0.21 |
| *B. longum* | |
| Bacteria control | 0.005 |
| G-W/W (0.025% w/v) | 0.35 |
| G-W (0.025% w/v) | 0.15 |
| Instant tea (0.025% w/v) | 0.10 |

Flavor tests of Gyokuro water/water extract, Gyokuro-$H_2O$/ButOH/$H_2O$ extract and instant ice tea were carried out. The test was performed with four volunteers.

Gyokuro water/water extract and Gyokuro-$H_2O$/ButOH/$H_2O$ extract were characterized as having relatively little or no taste or smell compared to instant ice tea.

While the invention has been described above in some detail for purposes of illustration, variations will be readily apparent to those skilled in the art. Thus, the present invention is to be defined as set forth in the following claims.

We claim:

1. A process of preparing an extract of *Camellia sinesis* having Bifidobacterium growth-promoting properties comprising:
   (a) extracting *C. sinesis* leaves with water or a water-miscible organic solvent, to provide a solution comprising dissolved solids;
   (b) extracting an aqueous solution of said dissolved solids with at least one polar organic solvent immiscible with water to provide an organic phase and an aqueous phase; and
   (c) separating said aqueous phase from said organic phase and recovering the dissolved solids in said aqueous phase to yield an extract of *C. sinensis*.

2. A process according to claim 1 wherein said leaves are green tea leaves.

3. A process according to claim 1 wherein said leaves are Oolong tea leaves.

4. A process according to claim 1 wherein said leaves are black tea leaves.

5. A process according to claim 1 wherein said polar organic solvent is selected from the group consisting of chloroform, ethyl acetate and butanol.

6. A process according to claim 5 wherein said polar organic solvent is butanol.

7. A process according to claim 1 wherein said aqueous solution of said dissolved solids is sequentially extracted with more than one polar organic solvent.

8. A process of preparing an extract from *Camellia sinensis* and Bifidobacterium growth-promoting properties comprising:
   (a) extracting *C. sinensis* leaves with hot water to provide an aqueous leaf extract comprising dissolved solids;
   (b) extracting an aqueous solution of said dissolved solids with at least one polar organic solvent immiscible with water to provide an organic solvent phase and an aqueous product phase; and
   (c) separating said aqueous product phase from said organic phase and recovering the dissolved solids in said aqueous product phase to yield an extract from *C. sinensis*.

9. A process according to claim 8 wherein said polar organic solvent is selected from the group consisting of chloroform, ethyl acetate and butanol.

10. A process according to claim 8 wherein said dissolved solids in said aqueous product phase are recovered and dissolved in water.

11. A process according to claim 10 wherein said polar organic solvent is selected from the group consisting of chloroform, ethyl acetate and butanol.

12. A process according to claim 10 wherein said dissolved solids in said aqueous leaf extract are recovered by freeze-drying.

13. A solid composition for promoting the growth of Bifidobacterium comprising the recovered dissolved solids in said aqueous product phase of claim 8.

14. A process of preparing an extract from *Camellia sinensis* having Bifidobacterium growth-promoting properties comprising:
   (a) extracting *C. sinensis* leaves with hot water to provide an aqueous leaf extract and leaf residue;
   (b) extracting said leaf residue with a water-miscible solvent to yield an aqueous crude product comprising dissolved solids;
   (c) extracting said aqueous crude product with at least one polar organic solvent immiscible with water to provide an organic solvent phase and an aqueous product phase; and
   (d) separating said aqueous product phase from said organic solvent phase and recovering the dissolved solids in said aqueous product phase to yield an extract from *C. sinensis*.

15. A process according to claim 14 wherein said dissolved solids in said aqueous product phase are recovered and dissolved in water.

16. A process according to claim 15 wherein said dissolved solids in said aqueous product phase are recovered by freeze-drying.

17. A process according to claim 14 wherein said water-miscible solvent is an alcohol and said leaf residue is extracted with said alcohol.

18. A process according to claim 17 wherein said alcohol is ethanol.

19. A process according to claim 18 wherein said polar organic solvent is selected from the group consisting of chloroform, ethyl acetate and butanol.

20. A process according to claim 18 wherein said dissolved solids in said aqueous product phase are recovered by freeze-drying.

21. A process according to claim 17 wherein said polar organic solvent is selected from the group consisting of chloroform, ethyl acetate and butanol.

22. A solid composition for promoting the growth of Bifidobacterium comprising the recovered dissolved solids from said aqueous phase of claim 1.

23. A solid composition for promoting the growth of Bifidobacterium comprising the recovered dissolved solids in said aqueous product phase of claim 14.

24. A substantially flavorless composition that promotes the growth of Bifidobacterium comprising the water-soluble solids of *Camellia sinensis* leaves substantially free of solids that are also soluble in a water-immiscible polar organic solvent.

25. A method of promoting the growth of Bifidobacterium comprising contacting Bifidobacterium with an effective amount of the composition of claim 24.

* * * * *